United States Patent
Varnes (10) Patent No.: US 8,123,522 B2
(45) Date of Patent: Feb. 28, 2012

(54) DENTAL HANDPIECE FLUID SUPPLY TECHNOLOGY

(75) Inventor: DeWayne L. Varnes, Ridgeland, WI (US)

(73) Assignee: Mark L. Anderson, Spring Valley, WI (US)

( * ) Notice: Subject to any disclaimer, the term of this patent is extended or adjusted under 35 U.S.C. 154(b) by 581 days.

(21) Appl. No.: 12/221,594

(22) Filed: Aug. 5, 2008

(65) Prior Publication Data

US 2010/0035204 A1 Feb. 11, 2010

(51) Int. Cl.
*A61C 1/10* (2006.01)

(52) U.S. Cl. .......................................... 433/84; 433/100

(58) Field of Classification Search .................. 433/80, 433/84–85, 87, 99–101, 82, 98; 137/107, 137/561 A, 592, 595, 861
See application file for complete search history.

(56) References Cited

U.S. PATENT DOCUMENTS

| | | | |
|---|---|---|---|
| 2,420,338 A * | 5/1947 | Page | ............................ 433/84 |
| 4,117,861 A | 10/1978 | Betush | |
| 4,217,101 A | 8/1980 | Loge | |
| 4,470,812 A * | 9/1984 | Martens et al. | .................. 433/85 |
| 4,676,750 A * | 6/1987 | Mason | .......................... 433/101 |
| 4,973,247 A | 11/1990 | Varnes et al. | |
| 5,261,816 A | 11/1993 | Varnes | |
| 5,295,825 A | 3/1994 | Betush | |
| 5,360,338 A | 11/1994 | Waggoner | |
| 5,700,147 A * | 12/1997 | Mills et al. | ...................... 433/98 |
| 5,836,483 A | 11/1998 | Disel | |
| 2002/0170607 A1 | 11/2002 | Chang et al. | |

FOREIGN PATENT DOCUMENTS

WO PCT/CA00/00071 8/2001

* cited by examiner

*Primary Examiner* — Cris L Rodriguez
*Assistant Examiner* — Hao D Mai
(74) *Attorney, Agent, or Firm* — Skinner & Associates (57) ABSTRACT

A dental fluid delivery system for use with a dental drill is disclosed. The dental fluid delivery system includes a coolant water supply, a drive air line, a water line, and a coolant mist air controller. The coolant water supply unit includes a controller and a water container. The controller has a drive air inlet, a water inlet communicatively connected to the water container, a drive air outlet, and a water outlet. The drive air line is connected to the drive air outlet of the water supply unit. The water line is connected to the water outlet of the water supply unit. The coolant mist air controller is connectable in use to a dental drill. The mist air controller has a drive air inlet, a drive air outlet, a water inlet, a water outlet, and a mist air outlet.

10 Claims, 8 Drawing Sheets

DENTAL HANDPIECE FLUID SUPPLY TECHNOLOGY

CROSS-REFERENCE TO RELATED APPLICATIONS, IF ANY

Not applicable.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND

1. Field

The present invention relates, generally, to dental apparatus and methods. More particularly, the invention relates to dental drills, irrigators and air supplies. Most particularly, the invention relates to a system, apparatus and methods for providing drive, coolant, irrigation liquids, and mist air in a dental handpiece. The techniques of the invention can also be used in other fields such as medical and veterinary medical apparatus and methods.

2. Background Information

Dental hand pieces may provide means for drilling, drilling coolant, irrigation, mist air, air, and combinations thereof.

High speed drills and the like used in preparing teeth for filings and other work require that such equipment be kept at a temperature sufficient to not overheat while in the patient's mouth. High speed drills generate heat from friction as the drill contacts a tooth. Contact with a hot drill could burn delicate oral tissue. To minimize this problem, hand pieces typically utilize a coolant spray or mist, commonly water spray or mist, that encompasses the work area and is emitted from the distal end of the handpiece.

A problem which can occur in apparatus is backflow of saliva, blood, bacteria or other liquids from the mouth of the patient into the reservoir which houses the coolant. Apparatus such as those disclosed in U.S. Pat. Nos. 5,261,816; 5,261,816 and 4,973,247 may permit a backflow event which may potentially result in contamination of coolant and subsequent transfer of contaminated liquid mixture to patients. Disposable or sterilizable containers disclosed in the latter two patents may aid in avoiding such transfer of contaminated material.

Another potential problem that may occur is excess coolant flow after a handpiece is deactivated. This may cause a poor work field, inconvenience for the dentist, and discomfort for the patient.

Thus, to avoid this problem, mist air is desirable in certain dental procedures. However, mist air, or any air disturbance may embed debris in soft oral tissue. Therefore, coolant/mist should be carefully controlled.

Microbial conditions of compressed air often cannot be completely assured. Thus, when sterile procedures are recommended, mist air should be shut off completely and sterile irrigant (for example water) used in it's place. Some leakage of air may still occur through the turbine bearing on some handpieces. This can be minimized by not having an exhaust tube on the handpiece which improves free flow of air. Alternatively, a handpiece may be run on an inert gas such as Nitrogen.

Some microorganisms, including those found on dental handpieces maybe resistant to chemical disinfection. Therefore, autoclave (heat and pressure) disinfection or sterilization is desirable. A complete handpiece system, including the Handpiece, Water Line and Water/Water Container, that is amenable to autoclave disinfection and use in the sterile zone is desirable. It is particularly beneficial that the entire system be operable by the user with gloves on.

For these and other reasons, a need exists for the present invention.

All US patents and patent applications, and all other published documents mentioned anywhere in this application are hereby incorporated by reference in their entirety.

BRIEF SUMMARY

The present invention provides a dental apparatus and method that is practical, reliable, accurate and efficient, and that is believed to fulfill a need and to constitute an improvement over the background technology.

In one aspect, the invention provides a dental fluid delivery system for use with a dental drill, comprising a coolant water supply, a drive air line, a water line, and a coolant mist air controller. The coolant water supply unit includes a controller and a water container, the water controller having a drive air inlet, a water inlet communicatively connected to the water container, a drive air outlet, and a water outlet. The drive air line is connected to the drive air outlet of the water supply unit. The water line is connected to the water outlet of the water supply unit. The coolant mist air controller is adapted for connection to a dental drill, the mist air controller having a drive air inlet, a drive air outlet, a water inlet, a water outlet, and a mist air outlet.

In another aspect, the invention provides a coolant water supply unit for use with a dental fluid delivery system of a dental drill, comprising a controller having a drive air inlet, a water inlet, a drive air outlet, a water outlet; and a water container connected to the water inlet.

And in a further aspect, the invention provides a coolant mist air controller for use with a dental fluid delivery system of a dental drill, comprising a body adapted for connection to a dental drill, the body having a drive air inlet, a drive air outlet, a water inlet, a water outlet, and a mist air outlet.

The aspects, features, advantages, benefits and objects of the invention will become clear to those skilled in the art by reference to the following description, claims and drawings.

BRIEF DESCRIPTION OF THE SEVERAL VIEWS OF THE DRAWING

The present invention, and the manner and process of making and using it, will be better understood by those skilled in the art by reference to the following drawings.

DETAILED DESCRIPTION

Figure 1:
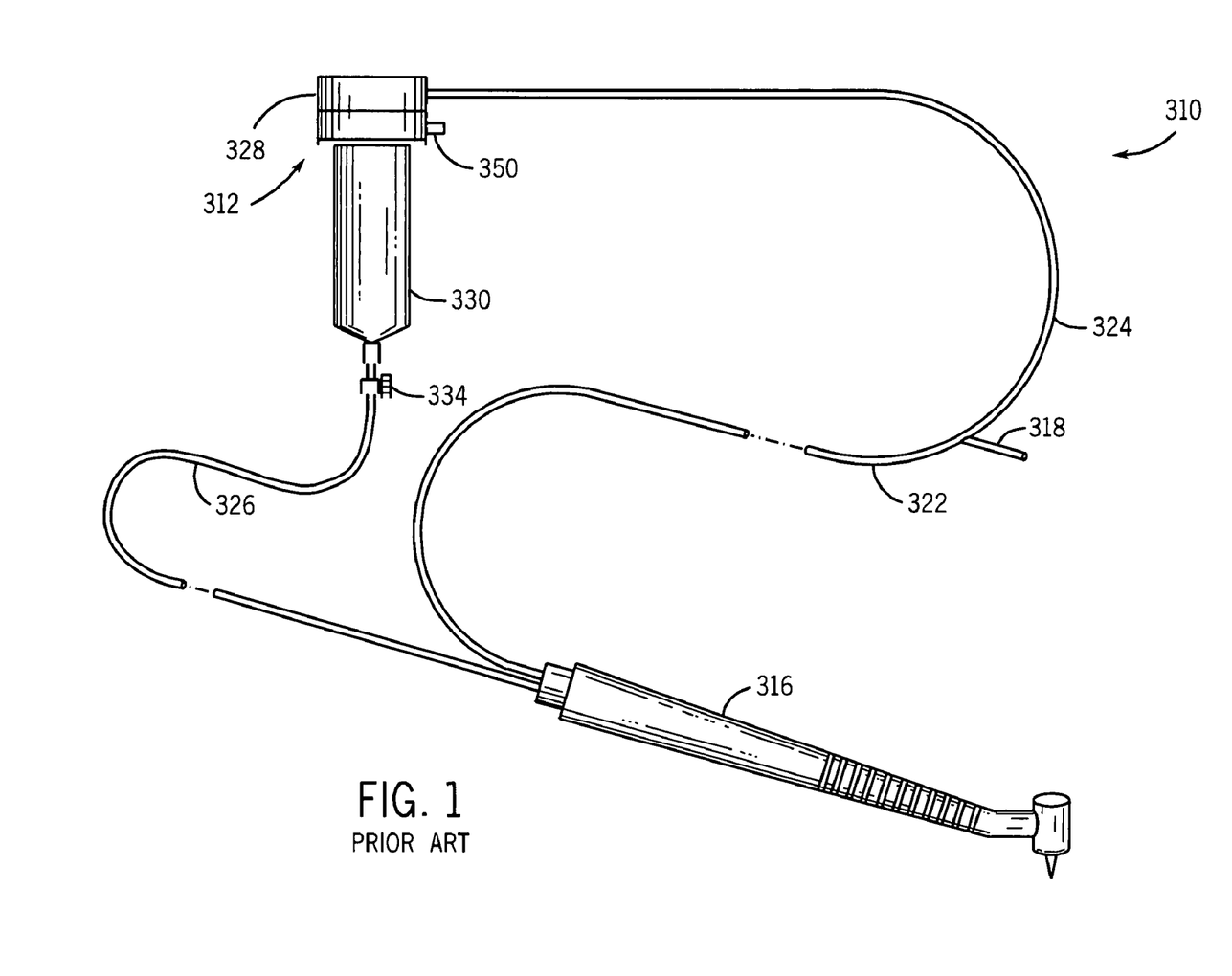
FIG. 1 is a diagram showing a dental handpiece drive system including applicant's prior art coolant delivery system.

Referring to FIG. 1, a prior art dental handpiece drive system 310 is illustrated and includes a prior art coolant delivery system 312 disposed between a conventional pressurized-gas (air) source (not shown) and a conventional handpiece 316 and is operated by a conventional, selectively-operable, closable valve activated by a foot pedal (not shown) as known in the art. The pressurized-gas line 318 has two branches 322, 324, with the first branch 322 thereof leading directly to the handpiece 316 to thereby operate a conventional turbine drive in the handpiece as known in the art within the handpiece 316. The second branch 324 of the pressurized-gas line 318 leads to the coolant delivery system 312 for pressurization of coolant therein and ultimate delivery therefrom through a conduit 326 to the handpiece 316. The coolant delivery system 312 includes a pressurized-gas distribution structure 328 and a removable reservoir 330 where coolant, for example water, is housed. Desired coolant flow volume from the reservoir 330 can be regulated by a conventional hand-operable screw clamp closure 334, as known in the art, placed on the conduit 326. Coolant flow volume is usually calibrated by the dentist who sets the screw clamp closure 334 for desired coolant flow at maximum turbine drive magnitude. In this manner, flow volume is reduced at lower turbine speed and increases to maximum flow velocity when the turbine drive is operated at fall speed. The coolant delivery system 312 can be mounted to a stand, work table or the like for convenient placement near a patient.

Figures 2, 3:
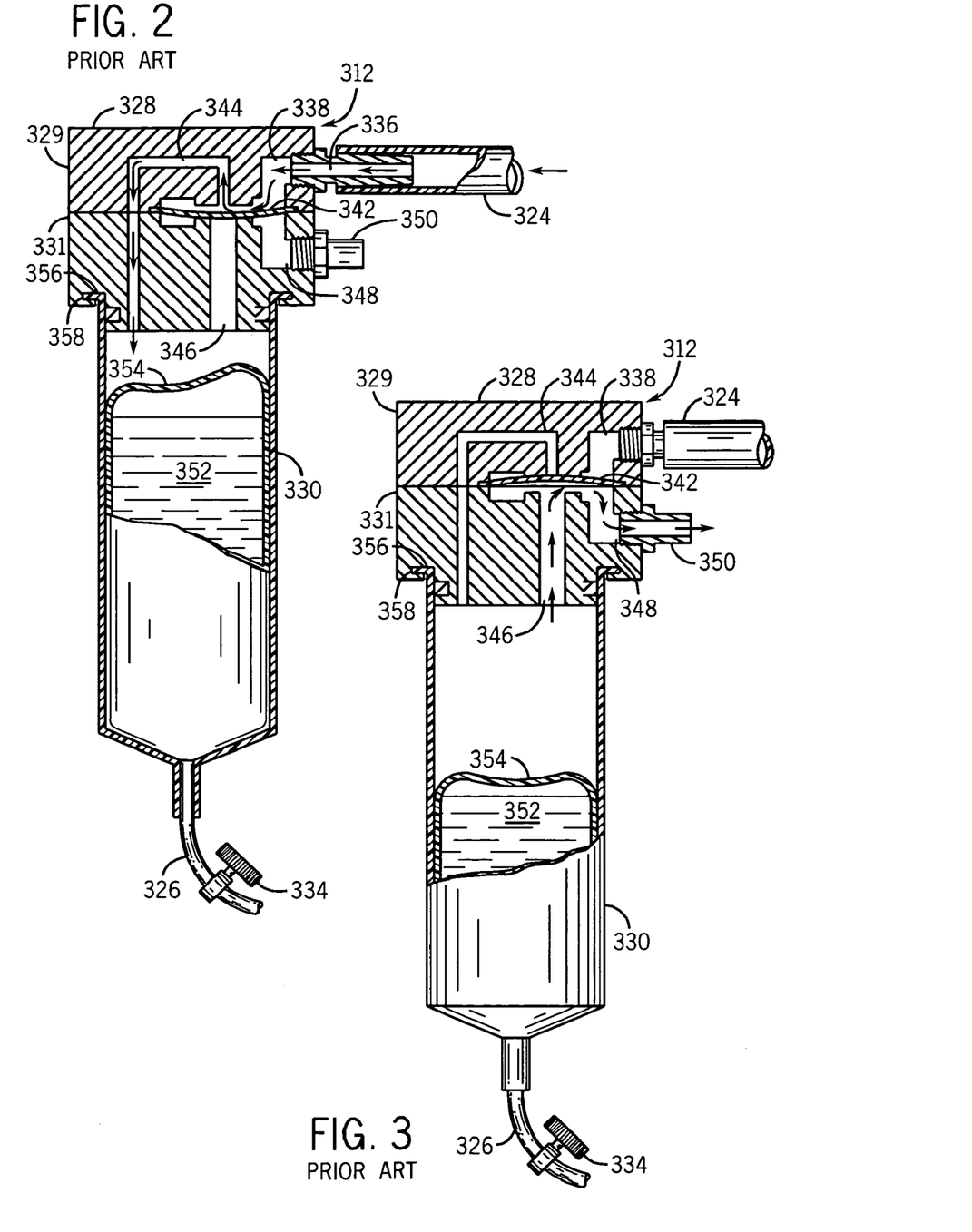
FIG. 2 is a crossectional view of the prior art coolant delivery system in operation.
FIG. 3 is a crossectional view of the prior art coolant delivery system immediately upon cessation of operation.

FIGS. 2 and 3 show the prior art pressurized-gas distribution structure 328 and reservoir 330 in section. The structure 328 is constructed of an upper piece 329 and a lower piece 331 secured to each other by conventional screws. An entry port 336 accepts the second branch 324 of the pressurized-gas line 318 and permits gas, for example air, entry into a pressurized-gas entry chamber 338 when the foot pedal is activated by the dentist. The structure 328 is provided with a first passage 344 leading from the chamber 338 to the reservoir 330; a second passage 346 leading from the reservoir 330 back to the chamber 338; and a third passage 348 leading to the exterior via an exit port 350. The cross-section dimension (diameter) of the first passage 344 is here shown at about one-third the cross-section dimension of the entry chamber 338 so that a Venturi effect occurs to thereby increase gas pressure entering the reservoir 330. The cross-section dimension of the first passage 344 is no greater than about 50%, typically between 25% and 50%, of the diameter of the entry chamber 338 so that gas entering the reservoir 330 is adequately pressurized. The cross-section dimension of the second passage 346 is larger than that of the first passage 344. A flexible circular membrane 342, typically constructed of silicone rubber and secured in place at its border between the upper piece 329 and lower piece 331 of the structure 328, overlays the openings of the second and third passages 346, 348 in the chamber 338. The reservoir 330 can directly house coolant. Coolant 352 can also be disposed within a flexible and collapsible bladder 354 from which the conduit 326 extends. The bladder 354 and conduit 326 may be disposable, be of one-piece construction, and be provided to the dentist with coolant 352 in place therein. The dentist then removes the reservoir 30 from the structure 328 and places the bladder 354 within the reservoir 330 after guiding the conduit 326 out the bottom of the reservoir 330. Thereafter, the reservoir is once again secured to the gas distribution structure 328 and the coolant 352 within the bladder 354 has not been subjected to possible contamination. The amount of coolant is preferably from about 30 to 50 ml. Attachment of the reservoir 330 to the gas distribution structure 328 can be by any suitable means as would be recognized in the art to achieve an air-tight fit. The reservoir 30 is constructed as a conventional syringe body having opposing laterally-extending flanges 356 which fit within laterally opposing complimentary horizontal retainer grooves 358 at the base of the gas distribution structure 328. The reservoir 330 is thereafter positioned so that a quarter-turn rotation of the reservoir 30 locks the reservoir in place.

In operation, when pressurized gas enters the chamber 338 via the entry port 336, it is immediately diverted downwardly as illustrated by the arrows in FIG. 3 to strike the top surface of the flexible membrane 342 to force the membrane 342 against the openings of the second and third passages 346, 348 and thereby close these passages. The gas flows through the first passage 344 into the reservoir 330 where it pressurizes the reservoir for resultant coolant exit into and through the conduit 326 and delivery to the handpiece 316. Because the second and third passages 346, 348 are blocked by the membrane 342 while gas is flowing, the reservoir is maintained in a pressurized state.

Figure 4:
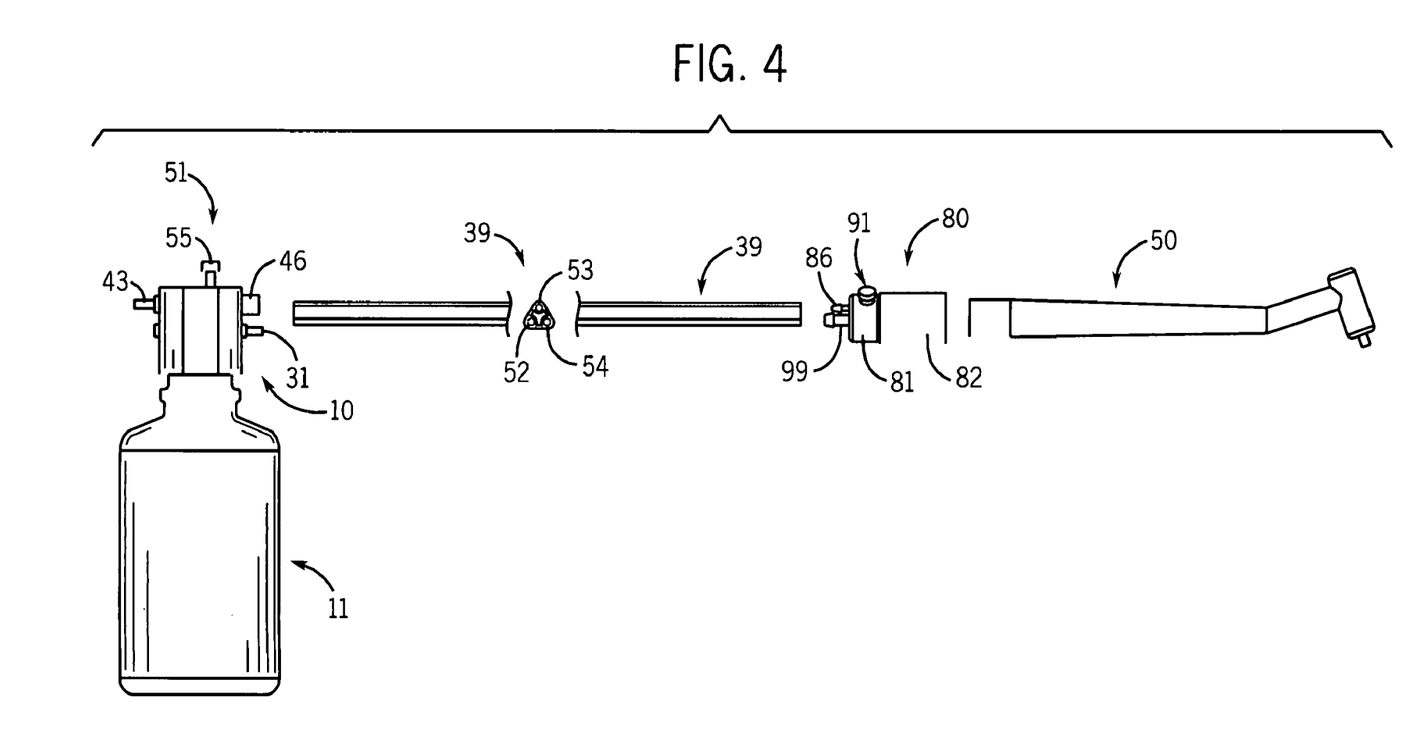
FIG. 4 illustrates an embodiment of the fluid supply system of the present invention for use with a dental handpiece, and including embodiments of a water supply unit and a mist air unit of the present invention.

Referring to FIG. 4, a preferred embodiment of the dental handpiece fluid supply system of the invention is shown. The system includes a mist air controller 80 operatively connected to a conventional handpiece 50, and a liquid coolant or water supply unit 51. A liquid coolant (typically water) supply hose 53 and a gas (typically air) supply hose 52 extend from the liquid coolant supply unit 51 to the mist air controller 80. A pressurized gas (also typically air) hose extends from a conventional gas supply means (not shown), typically a foot controller and a compressor. The system components can all be placed in an autoclave or the like for sterilization.

Figures 5, 6:
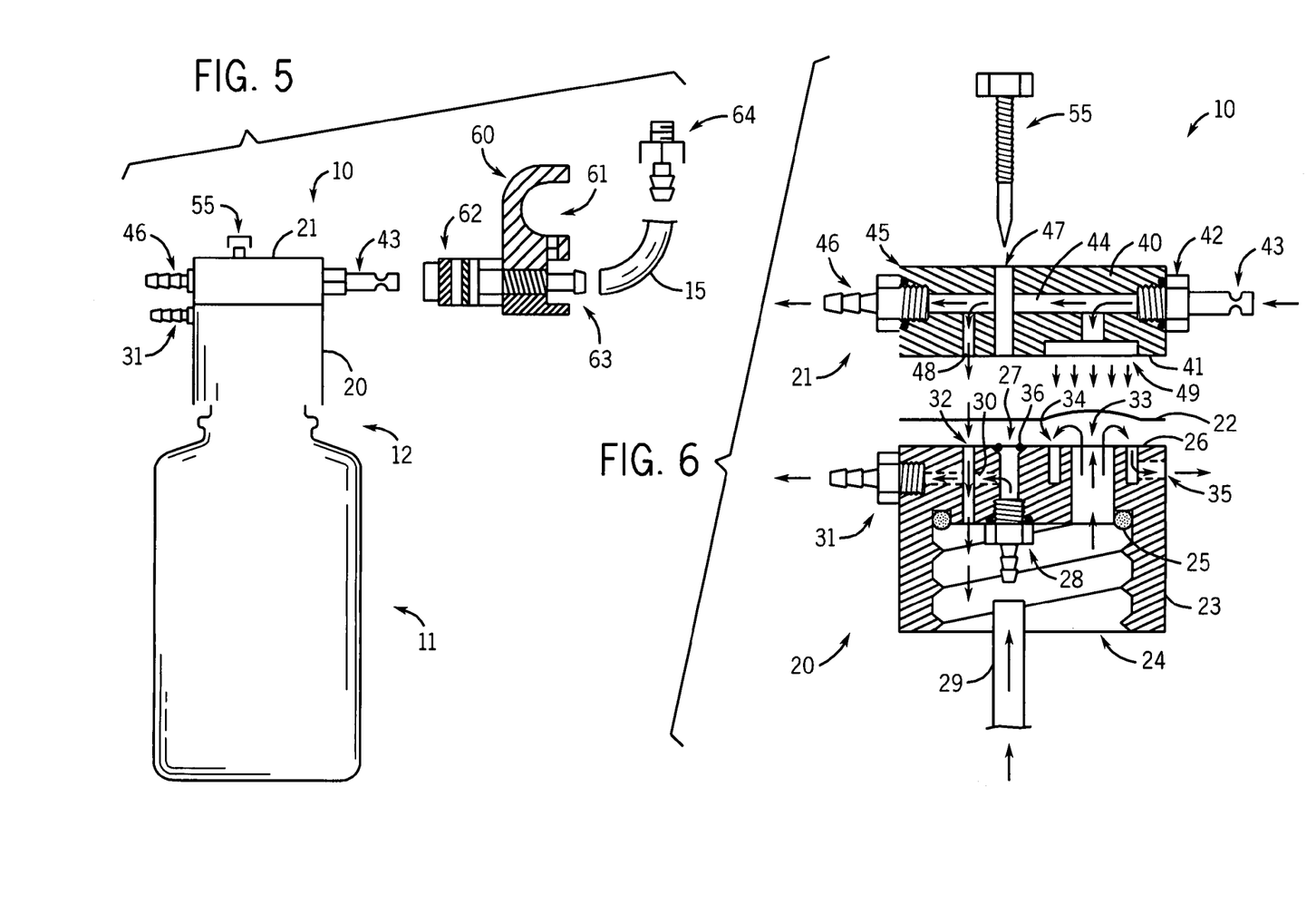
FIG. 5 is a view of an embodiment of the water supply unit of the invention, including embodiments of a water supply controller, a water holder, and an optional hanger adapter.
FIG. 6 is a crossectional view of the water supply controller, separated into top and bottom members.

Referring to FIGS. 5 and 6, a preferred embodiment of the liquid coolant supply unit 51 includes a fluid controller 10, a container 11, and optional hanger 60. The container 11 preferably has a bottle configuration and holds a predetermined quantity of liquid, preferably sterile water. In the example shown, the container 11 holds approximately 4.0 oz. (118.3 ml.) of liquid. The container 11 preferably has a threaded top or neck 12, which connects with a threaded receiver 24 on the connector 10. The controller 10 controls the distribution or delivery of fluids, gasses and liquids. It has a gas input fitting 43 which connects with the gas supply line 15. Preferably, fitting 43 is a quick connect fitting which mates with the optional, intermediary, hanger 60, and the hanger 60 is connected to the gas supply line 15. The hanger 60 preferably has a quick connect fitting which complements the fitting 43 of the controller 10. Hose fitting 63 connects with the line 15. Curved arm 61 connects to a standard dental tool holder (not shown). Hose line 15 connects to an air supply or foot controller (not shown) via a fitting 64. Controller 10 further includes a gas exit fitting 46 and a liquid exit fitting 31. Liquid flow adjuster screw 55 is disposed in the top of the connector 10 for regulating the flow of coolant liquid to the handset drill 50. Screw 55 has a hand knob at its top which is exposed for manual manipulation by the user, a threaded portion below the knob that is seated in threaded bore 47, and a tapered bottom that is adjustably disposed in bore 27 to vary the size of the opening to exit bore 30. This sterile arrangement is easy to hold, manipulate and adjust by a gloved user.

As is best shown in FIG. 6, the liquid coolant supply controller 10 is preferably constructed of a bottom member or base 20 and a top member or cap 21 which are operatively attached to each other. A diaphragm 22 is disposed between bottom connection surface 41 of the top member 21 and the top connection surface 26 of the bottom member 22.

Figure 7:
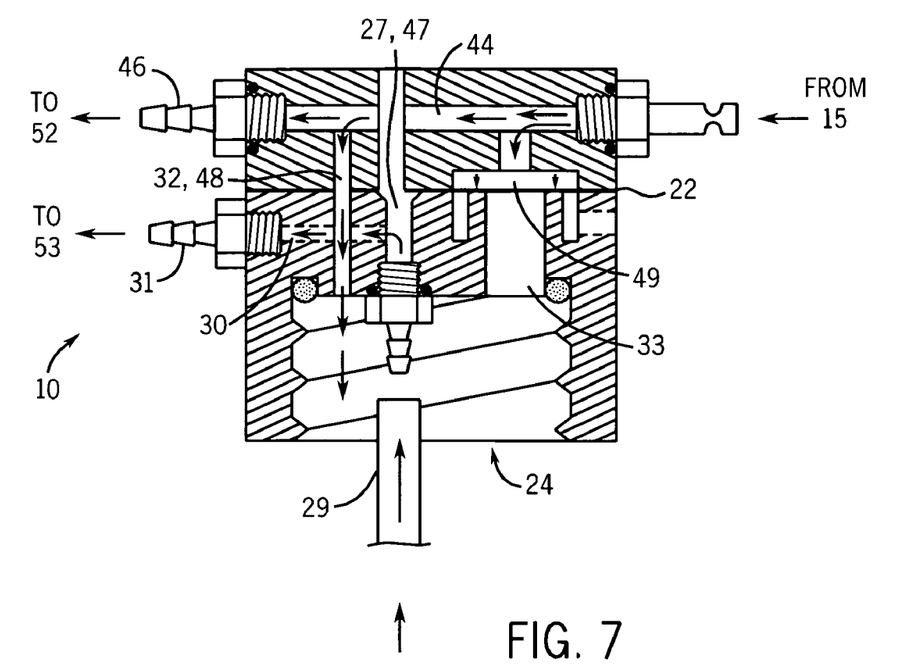
FIG. 7 is view of the water supply controller illustrating one stage of use.
Figure 8:
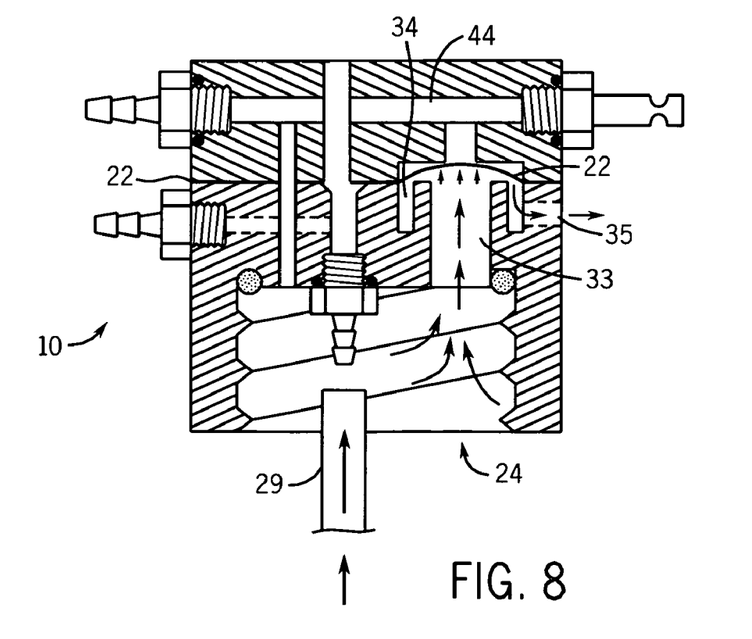
FIG. 8 is a view of the water supply controller illustrating another stage of use.
Figure 9:
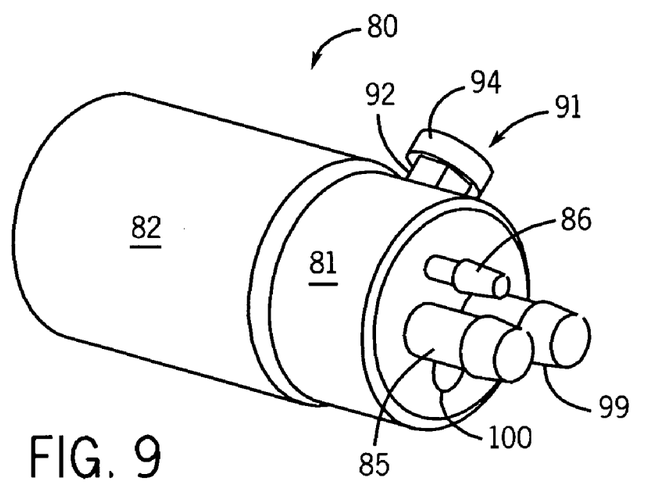
FIG. 9 is a perspective view of an embodiment of the mist air unit of the present invention.
Figure 10:
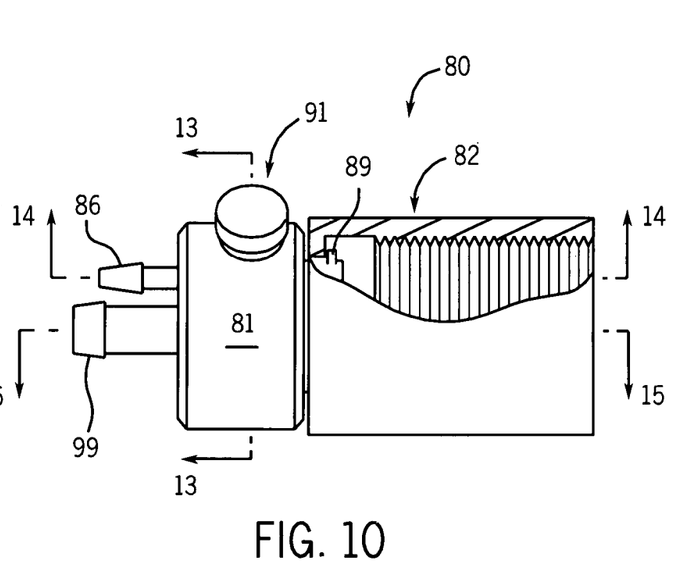
FIG. 10 is a side view of the mist air unit.
Figure 11:
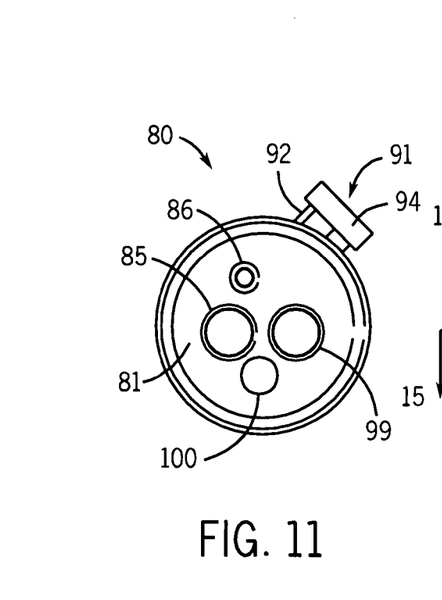
FIG. 11 is an end view of the mist air unit.
Figure 12:
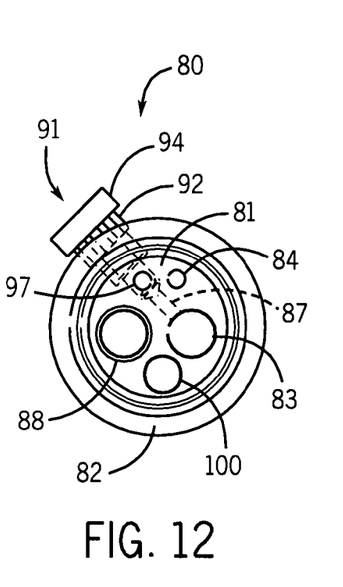
FIG. 12 is an opposite end view of the mist air unit.
Figure 13:
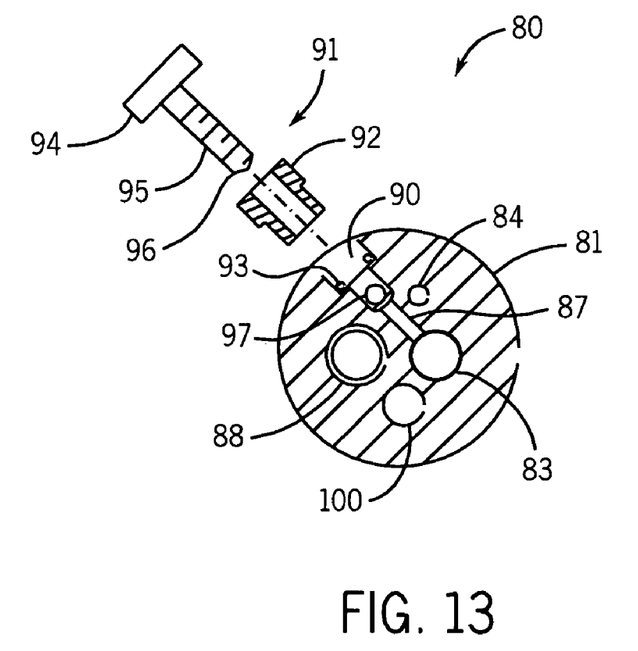
FIG. 13 is a crossectional view of the mist air unit taken along line 13-13 of FIG. 10.
Figure 14:
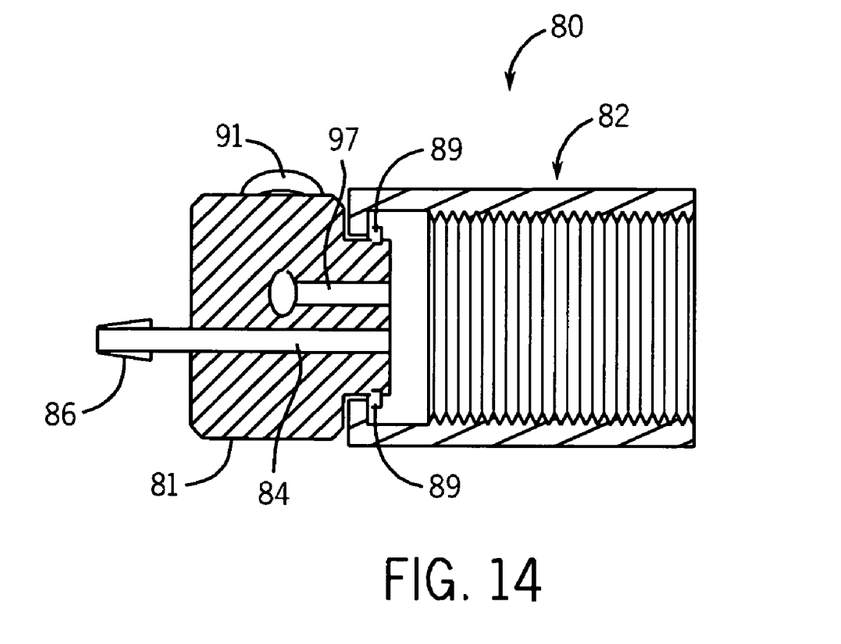
FIG. 14 is a crossectional view of the mist air unit taken along line 14-14 of FIG. 10.
Figure 15:
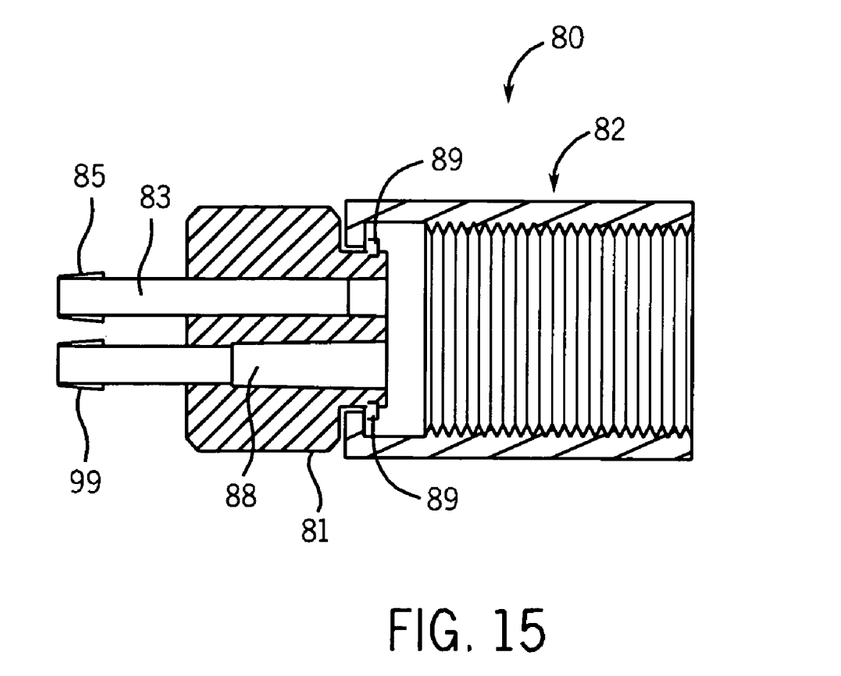
FIG. 15 is a crossectional view of the mist air unit taken along line 15-15 of FIG. 10.

Referring also to FIGS. 7 and 8, the bottom member or base 20 has a body 23 constructed of a rigid material, preferably a metal such as stainless steel, and has a generally cylindrical configuration. In the embodiment shown, the bottom member 21 has a diameter of about 0.400 in. and a width or thickness of 0.345 in; at its widest aspect, the periphery of the cylinder. The threaded receiver 24 is disposed centrally in the bottom of the member 20. Bore 27 extends vertically (as shown in the drawing) from the end of the threaded receiver 24 to the top surface 26. Bore 30 extends substantially at a right angle (horizontally with respect to the drawing) from the side of the body 23 to the bore 27 and functions in cooperation with bore 27 to permit egress of liquid from container 11. Hose fitting 28 is disposed at the bottom end of the bore 27 for connection of a predetermined length of hose 29. Hose 29 preferably extends substantially the length of container 11 and is for facilitating egress of liquid therefrom. O-ring 36 is disposed about the top of the bore 27. Bore 33 is disposed to the side of bore 27 and extends vertically (again with respect to the drawing) from the end of receiver 24 to the top surface 26. Annular bore 34 is disposed a predetermine depth coaxially with respect to bore 33. Exhaust port 35 extends substantially at a right angle (horizontally in the drawing) from annular bore 34 to exhaust at the side of the body 23.

The top member or cap 21 has bottom connection surface 41 which mates with the top connection surface 26 of bottom member 20, with the diaphragm 22 disposed therebetween. The top member 21 and bottom member 20 are preferably connected by bolts or screws. Top member 21 has a body 40 constructed of a rigid material which is the same as or complementary to that of bottom member 20, preferably a metal such as stainless steel. Top member 21 also has a generally cylindrical configuration. In the embodiment shown, the top member 21 has a diameter equal to that of the bottom member 20. Bore 47 extends vertically (as shown in the drawing) through the body 40 from a bottom connection surface 41 to the its top surface. Bore 47 has a diameter which is preferably equal to that of bore 27 in bottom member 20. Bore 44 extends horizontally (with respect to the drawing) through the body and functions to permit passage of air through the connector 10. Bore 48 is communicatively connected to bore 44 and extends downwardly therefrom to exit at bottom connection surface 41 where it is aligned for communicative connection with bore 32 of bottom member 20. Thus, air passing through bore 44 may be used to pressurize the interior of container 11 as described further below. Bore 48 preferably has a diameter equal to that of bore 32 of bottom member 20. Fitting 43 (with connection nut 42) is disposed at one end of the bore 44 for connection to an adapter or directly to an air supply or air supply hose. Hose fitting 46 with connection nut 45 is disposed at the opposite end of the bore 44. Bore 49 is disposed to the side of bore 47 and extends substantially at a right angle (vertically with respect to the drawing) from bore 44 to the bottom connection surface 41. In this embodiment, bore 49 has a top portion with a diameter sufficient to hold the water supply bottle 11, and a bottom portion with a diameter equal to the outside diameter of annular bore 34 in bottom member 20. The diameter and thickness or height of the bottom portion of the bore 49 is sufficient to permit deflection of the diaphragm 22.

In operation, pressurized gas (typically air) from line 15 (typically under control of a foot pedal or the like) enters horizontal first bore or channel 44 of the controller 10 and flows through it to gas line 52, attached to fitting 46, to provide air to turn the turbine on handset drill 50. At the same time, the pressurized gas flowing through bore 44 enters vertical second bore or channel 48/32 to chamber 24 and into the interior of container 11. The input gas pressurizes the container 11 and causes contained liquid (water) to flow out of the container 11 up hose 29 through vertical third bore 47/27 to horizontal fourth bore or channel 30 and exit via liquid line 53 attached to fitting 31. Simultaneously, pressurized gas in bore 44 flows into vertical fifth bore or channel 49 and deflects membrane 22 sealingly downwardly to block sixth bore 33 for sealing and maintaining a pressurized state in container 11. Adjuster 55 may be manipulated by the user to turn on/off and vary the flow of liquid coolant from the coolant controller 10.

When the flow of pressurized gas ceases, for example via foot pedal actuation, pressure from gas in fifth bore 49 ceases to push membrane 22 downwardly. This permits pressure in the chamber 11 to deflect membrane 22 upwardly. Pressure in the chamber 11 then exits annular port 34 and out to the atmosphere via exhaust vent 35. This shuts off the flow of liquid coolant in synchronization with cessation of turbine gas.

Referring to FIGS. 9-15, the mist air controller 80 controls mixing of turbine air and liquid (water) from the liquid supply unit 10 to create mist air for cooling the drill or dental handpiece 50. The mist air controller 80 utilizes standard turbine drive air and does not require a separate air system. It is therefore easily sterilizable. It has a body 81 constructed of a rigid material, preferably a metal such as stainless steel, and has a generally cylindrical configuration. The threaded handpiece receiver 82 is disposed one side of the controller 80 and is connectable to a standard dental handpiece as shown for example in FIG. 4. The dental handpiece 50 has a burr tool that is driven by air input from the controller 80 to the burr turbine. Turbine air is input and exhausted as described further below via the mating of complementary ports. The dental handpiece 50 also has a water output, air output and light outputs which are communicatively connected to the controller 80 by complementary ports that are also described in more detail below. During use of the handpiece, a water stream can be added and impact the burr for cooling and for removing debris from the work site. Coolant air (mist air) can be added to turn the stream into a forceful spray.

Drive or turbine air supply port 83 extends longitudinally as a bore or channel in the body 81 from the end of the threaded receiver 82 (output end) to the opposite end (input end). Hose fitting 85 is disposed at the input end of the bore 83 for connection to drive air supply 52 in hose 39. Drive or turbine air exhaust port 88 extends longitudinally as a bore or channel from the output end to the input end of the body 81.

Hose fitting 99 is disposed at the input end of the bore 88 for connection to the drive air exhaust channel 54 of hose 39.

Water port 84 extends longitudinally through the body 81 from the end of receiver 82 to the opposite end. Hose fitting 86 is disposed at the input end of the bore 84 for connection to liquid supply 53 of hose 39.

Mist air port 97 extends longitudinally as a bore or channel from the end of the receiver 82, a predetermined distance through the body 81 towards the input end. Bore or channel 87 extends generally transversely from the drive air supply bore 83 to communicatively couple with mist air bore 97. Mist air flow adjuster 91 is disposed in the mist air controller 80 for regulating the flow of mist air to the handset drill 50 via mist air port 97. Adjuster 91 comprises a screw 95 and a nut 92. Screw 95 has a knurled hand knob 94 at its top which is exposed for manual manipulation by the user. Screw 95 has a threaded portion below the knob 94 that is disposed through the nut 92 which is seated in bore 90. Screw 95 has a tapered bottom portion 96 that is adjustably disposed to vary the size of the aperture and control mist air flow from port 97. O-ring 93 is preferably disposed at the bottom of bore 90. This sterile arrangement is easy to hold, manipulate and adjust by a gloved user.

Light port 100, for example a fiber optic arrangement, extends longitudinally from the end of the threaded receiver 82 to the input end of the body 81.

In operation, pressurized air from line 52 (via liquid coolant controller 51 and other associated dental apparatus) enters drive air input bore 83 and flows through it to drill 50, attached to fitting 82, to provide air to turn the drill turbine. With this controller 80, drive air flowing through bore 83 may also enter mist air bore 87. Adjuster 91 may be manipulated by the user to turn on/off and vary the flow of the mist air. Water flows into water input bore 84 and to the handpiece 50 to impact the handpiece burr without or without mist air.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A dental fluid delivery system for use with a dental hand drill including a drill end having a drill bit and a connection end having a water input, a drive air input and a mist air input, comprising:
   a. a coolant water supply unit including a controller and a water bottle, the controller having a drive air inlet adapted to be connected to a sole drive air supply for the system, a water inlet communicatively connected to the water bottle, a drive air outlet, and a water outlet;
   b. a single air input drive air line connected to the drive air outlet of the water supply unit;
   c. a water line connected to the water outlet of the water supply unit; and
   d. a portable, hand holdable coolant mist air controller adapted for connection to a dental drill, the coolant mist air controller being disposed at and carried with, when connected, the connection end of the hand drill, the mist air controller having a drive air inlet connected to the drive air line, a drive air outlet for connection to the drive air input of the dental hand drill, a water inlet connected to the water line, a water outlet for connection to the water input of the dental hand drill, a mist air outlet for connection to the mist air input of the dental hand drill, the mist air outlet being communicatively connectable with the drive air inlet to divert air therefrom for use in generating mist air.

2. The dental fluid delivery system of claim 1, wherein the controller has body that is connected to the top of the water bottle via a screw thread arrangement, the controller body having a first bore formed within the body which permits passage of drive air from an air inlet to an air outlet, a second bore formed within the body and extending from the first bore which permits of drive air into the water container, a third bore formed within the body and extending from the water container which permits passage of liquid from the container to the water outlet, and fourth and fifth bores formed within the body and separated by a flexible membrane which selectively controls communication between the fourth bore and an exhaust vent.

3. The dental, fluid delivery system of claim 2, wherein the controller further has an adjuster constructed and arranged to selectively vary the dimension of the fourth bore to control water output from the water supply unit.

4. The dental fluid delivery system of claim 1, wherein the coolant mist air controller has a cylindrical body having an input end and an output end, and further having a drive air input port extending axially through the body connecting the drive air line and the dental drill, a drive air exhaust port extending axially through the body and connected to the dental drill, a water port extending axially through the body and connecting the water line and the dental drill, a mist air port connected to the dental drill mist air input and extending axially into the body a predetermined distance, and an air diversion channel disposed transversely in the body and communicatively connecting the drive air input port to the axial mist air port.

5. The dental fluid delivery system of claim 4, wherein the coolant mist air controller further has an adjuster constructed and arranged to selectively control output of coolant mist air to the dental drill by controlling diversion of air through the transverse air diversion channel.

6. A coolant water supply unit for use with a dental fluid delivery system of a dental drill to control the supply of coolant water thereto, the dental drill being of the type having a single drive air supply line, comprising:
   a. a controller having a drive air inlet, a water inlet, a drive air outlet, and a water outlet, wherein the controller has a first bore which permits passage of drive air from an air inlet to an air outlet, a second bore extending from the first bore which permits of drive air into the water container, a third bore extending from the water container which permits passage of liquid from the container to the water outlet, and fourth and fifth bores separated by a flexible membrane which selectively controls communication between the fourth bore and an exhaust vent; and
   b. a water bottle connected to the water inlet.

7. The coolant water supply unit of claim 6, wherein the controller has a body that is connected to the top of the water bottle via a screw thread arrangement, the first bore being formed within the body the second bore being formed within the body and extending from the first bore he third bore being formed within the body and extending from the water container, and the fourth and fifth bores being formed within the body and separated by the flexible membrane.

8. A portable, hand holdable coolant mist air controller for use with a dental fluid delivery system of a dental hand drill the fluid delivery system being of the type having a single air input drive air line and a water supply line, the dental hand drill being of the type having a drill end including a drill bit, and a connection end including a water input, a drive air input and a mist air input, comprising a body adapted for connection to a dental drill and being disposed at and carried with the connection end of the hand drill, the body having a cylindrical configuration with an input end for connection to water and air supply means of a dental fluid delivery system, and an output end for connection to the dental drill, the body, a drive air inlet for connection to the drive air line, a drive air outlet for connection to the drive air input of the dental hand drill, a water inlet for connection to the water line, a water outlet for connection to the water input of the dental hand drill, a mist air outlet for connection to the mist air input of the dental drill, the mist air outlet being communicatively connectable with the drive air inlet to divert air therefrom to generate mist air.

9. The portable, hand holdable coolant mist air controller of claim 8, wherein the coolant mist air controller drive air inlet is connected to a drive air line and to a dental drill via a drive air input port extending axially through the body, the drive air outlet is connected to the dental drill via a drive air exhaust port extending axially through the body, the water inlet is connected to a waterline and to the dental drill via a water port extending axially through the body, the mist air outlet is connected to the dental drill via a mist air port extending axially into the body from the output end a predetermined distance, and an air diversion channel disposed transversely in the body communicatively connects the drive air input port to the axial mist air port.

10. The portable, hand holdable coolant mist air controller of claim 9, wherein the coolant mist air controller further has an adjuster constructed and arranged to selectively control output of coolant mist air to the dental drill by controlling diversion of air through the transverse air diversion channel.

* * * * *